US 9,808,582 B2

(12) United States Patent
Kramer et al.

(10) Patent No.: US 9,808,582 B2
(45) Date of Patent: *Nov. 7, 2017

(54) TWO-STAGE RECONSTITUTING INJECTOR

(71) Applicant: Antares Pharma, Inc., Minneapolis, MN (US)

(72) Inventors: Thomas E. Kramer, Coon Rapids, MN (US); Peter L. Sadowski, Woodbury, MN (US)

(73) Assignee: Antares Pharma, Inc., Ewing, NJ (US)

( * ) Notice: Subject to any disclaimer, the term of this patent is extended or adjusted under 35 U.S.C. 154(b) by 770 days.

This patent is subject to a terminal disclaimer.

(21) Appl. No.: 14/244,916

(22) Filed: Apr. 4, 2014

(65) Prior Publication Data

US 2014/0221916 A1    Aug. 7, 2014

Related U.S. Application Data

(63) Continuation of application No. 13/584,317, filed on Aug. 13, 2012, now Pat. No. 8,696,618, which is a
(Continued)

(51) Int. Cl.
*A61M 37/00* (2006.01)
*A61M 5/315* (2006.01)
(Continued)

(52) U.S. Cl.
CPC .......... *A61M 5/31596* (2013.01); *A61M 5/19* (2013.01); *A61M 5/2066* (2013.01);
(Continued)

(58) Field of Classification Search
CPC .............. A61M 5/2466; A61M 5/3202; A61M 2005/2013; A61M 2005/2073;
(Continued)

(56) References Cited

U.S. PATENT DOCUMENTS 547,370 A    10/1895  Chalefou
1,465,793 A    8/1923  Schilling
(Continued)

FOREIGN PATENT DOCUMENTS

AR    00081651    10/2012
AR    082053    11/2012
(Continued)

OTHER PUBLICATIONS

International Patent Application No. PCT/US14/23883, International Search Report, dated Jul. 10, 2014, 3 pages.
(Continued)

*Primary Examiner* — Jason Flick
(74) *Attorney, Agent, or Firm* — Morgan, Lewis & Bockius LLP

(57) ABSTRACT

An injector (10) for injecting a medicament into a patient. The injector includes a container (18) defining a first chamber (22), which contains a fluid therein, and a second chamber (23). The injector also includes an injection conduit (126) configured for directing the fluid fired from the container into the patient. A transfer mechanism is operable by a user to transfer the fluid from the first chamber to the second chamber in a first stage of operation, and a firing mechanism is operable by the user for firing the fluid from the second chamber through the injection conduit in a second stage of operation. An energy source (62) is in powering association with the firing mechanism to drive firing mechanism in the first and second stages.

17 Claims, 4 Drawing Sheets

Related U.S. Application Data continuation of application No. 12/299,274, filed as application No. PCT/US2007/067986 on May 2, 2007, now Pat. No. 8,251,947.

(60) Provisional application No. 60/796,939, filed on May 3, 2006.

(51) Int. Cl.
 *A61M 5/24* (2006.01)
 *A61M 5/32* (2006.01)
 *A61M 5/19* (2006.01)
 *A61M 5/30* (2006.01)
 A61M 5/20 (2006.01)
 A61M 5/31 (2006.01)

(52) U.S. Cl.
 CPC ............ *A61M 5/2466* (2013.01); *A61M 5/30* (2013.01); *A61M 5/3202* (2013.01); *A61M 5/2033* (2013.01); *A61M 5/3204* (2013.01); *A61M 5/326* (2013.01); *A61M 2005/2013* (2013.01); *A61M 2005/2073* (2013.01); *A61M 2005/2474* (2013.01); *A61M 2005/3125* (2013.01)

(58) Field of Classification Search
 CPC .. A61M 2005/2474; A61M 2005/3125; A61M 5/19; A61M 5/2033; A61M 5/2066; A61M 5/30; A61M 5/31596; A61M 5/3204; A61M 5/326
 USPC .......................................................... 604/82
 See application file for complete search history.

(56) References Cited

U.S. PATENT DOCUMENTS

| | | |
|---|---|---|
| 1,512,294 A | 10/1924 | Marcy |
| 1,687,323 A | 10/1928 | Cook |
| 2,354,649 A | 8/1944 | Bruckner |
| 2,607,344 A | 8/1952 | Brown |
| 2,645,223 A | 7/1953 | Lawshe |
| 2,648,334 A | 8/1953 | Brown |
| 2,687,730 A | 8/1954 | Hein |
| 2,688,967 A | 9/1954 | Huber |
| 2,699,166 A | 1/1955 | Bickinson |
| 2,717,601 A | 9/1955 | Brown |
| 2,728,341 A | 12/1955 | Roehr |
| 2,737,946 A | 3/1956 | Hein, Jr. |
| 2,813,528 A | 11/1957 | Blackman |
| 2,866,458 A | 12/1958 | Mesa et al. |
| 2,888,924 A | 6/1959 | Dunmire |
| 2,893,390 A | 7/1959 | Lockhart |
| 3,130,724 A | 4/1964 | Higgins |
| 3,166,069 A | 1/1965 | Enstrom |
| 3,375,825 A | 4/1968 | Keller |
| 3,382,865 A | 5/1968 | Worrall |
| 3,526,225 A | 9/1970 | Hayamamachi |
| 3,557,784 A | 1/1971 | Shields |
| 3,563,098 A | 2/1971 | Gley |
| 3,605,744 A | 9/1971 | Dwyer |
| 3,688,765 A | 9/1972 | Gasaway |
| 3,702,609 A | 11/1972 | Steiner |
| 3,712,301 A | 1/1973 | Sarnoff |
| 3,742,948 A | 7/1973 | Post et al. |
| 3,770,026 A | 11/1973 | Isenberg |
| 3,790,048 A | 2/1974 | Luciano et al. |
| 3,797,489 A | 3/1974 | Sarnoff |
| 3,797,491 A | 3/1974 | Hurschman |
| 3,811,441 A | 5/1974 | Sarnoff |
| 3,831,814 A | 8/1974 | Butler |
| 3,848,593 A | 11/1974 | Baldwin |
| 3,882,863 A | 5/1975 | Sarnoff et al. |
| 3,892,237 A | 7/1975 | Steiner |
| 3,895,633 A | 7/1975 | Bartner et al. |
| 3,946,732 A | 3/1976 | Hurscham |
| 4,031,893 A | 6/1977 | Kaplan et al. |
| 4,067,333 A | 1/1978 | Reinhardt et al. |
| 4,127,118 A | 11/1978 | Latorre |
| 4,171,698 A | 10/1979 | Genese |
| 4,222,392 A | 9/1980 | Brennan |
| 4,227,528 A | 10/1980 | Wardlaw |
| 4,258,713 A | 3/1981 | Wardlaw |
| 4,282,986 A | 8/1981 | af Ekenstam et al. |
| 4,316,463 A | 2/1982 | Schmitz et al. |
| 4,316,643 A | 2/1982 | Burk et al. |
| 4,328,802 A | 5/1982 | Curley et al. |
| 4,333,456 A | 6/1982 | Webb |
| 4,333,458 A | 6/1982 | Margulies et al. |
| 4,338,980 A | 7/1982 | Schwebel et al. |
| 4,373,526 A | 2/1983 | Kling |
| 4,378,015 A | 3/1983 | Wardlaw |
| 4,411,661 A | 10/1983 | Kersten |
| 4,484,910 A | 11/1984 | Sarnoff et al. |
| 4,529,403 A | 7/1985 | Kamstra |
| 4,553,962 A | 11/1985 | Brunet |
| 4,558,690 A | 12/1985 | Joyce |
| 4,573,971 A | 3/1986 | Kamstra |
| 4,592,745 A | 6/1986 | Rex et al. |
| 4,624,660 A | 11/1986 | Mijers et al. |
| 4,634,027 A | 1/1987 | Kanarvogel |
| 4,661,098 A | 4/1987 | Bekkering et al. |
| 4,662,878 A | 5/1987 | Lindmayer |
| 4,664,653 A | 5/1987 | Sagstetter et al. |
| 4,664,655 A | 5/1987 | Orentreich et al. |
| 4,678,461 A | 7/1987 | Mesa |
| 4,719,825 A | 1/1988 | LaHaye et al. |
| 4,722,728 A | 2/1988 | Dixon |
| 4,774,772 A | 10/1988 | Vetter et al. |
| 4,790,824 A | 12/1988 | Morrow et al. |
| 4,818,517 A | 4/1989 | Kwee et al. |
| 4,820,286 A | 4/1989 | van der Wal |
| 4,822,340 A | 4/1989 | Kamstra |
| 4,830,217 A | 5/1989 | Dufresne et al. |
| 4,874,381 A | 10/1989 | Vetter |
| 4,883,472 A | 11/1989 | Michel |
| 4,913,699 A | 4/1990 | Parsons |
| 4,915,701 A | 4/1990 | Halkyard |
| 4,929,238 A | 5/1990 | Baum |
| 4,936,833 A | 6/1990 | Sams |
| 4,940,460 A | 7/1990 | Casey et al. |
| 4,966,581 A | 10/1990 | Landau |
| 4,968,302 A | 11/1990 | Schluter et al. |
| 4,973,318 A | 11/1990 | Holm et al. |
| 4,976,701 A | 12/1990 | Ejlersen et al. |
| 4,982,769 A | 1/1991 | Fournier et al. |
| 4,986,816 A | 1/1991 | Steiner et al. |
| 5,042,977 A | 8/1991 | Bechtold et al. |
| 5,062,830 A | 11/1991 | Dunlap |
| 5,064,413 A | 11/1991 | McKinnon et al. |
| 5,069,670 A | 12/1991 | Vetter et al. |
| 5,078,680 A | 1/1992 | Sarnoff |
| 5,080,648 A | 1/1992 | D'Antonio |
| 5,080,649 A | 1/1992 | Vetter |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,388 A | 4/1992 | Richmond |
| 5,102,393 A | 4/1992 | Sarnoff et al. |
| 5,104,380 A | 4/1992 | Holman et al. |
| 5,114,406 A | 5/1992 | Gabriel et al. |
| 5,137,516 A | 8/1992 | Rand et al. |
| 5,137,528 A | 8/1992 | Crose |
| 5,139,490 A | 8/1992 | Vetter et al. |
| 5,163,907 A | 11/1992 | Szuszkiewicz |
| 5,176,643 A | 1/1993 | Kramer et al. |
| 5,180,370 A | 1/1993 | Gillespie |
| 5,185,985 A | 2/1993 | Vetter et al. |
| 5,195,983 A | 3/1993 | Boese |
| 5,221,348 A | 6/1993 | Masano |
| 5,226,895 A | 7/1993 | Harris |
| 5,232,459 A | 8/1993 | Hjertman |
| 5,256,142 A | 10/1993 | Colavecchio |

(56) References Cited

U.S. PATENT DOCUMENTS

| | | |
|---|---|---|
| 5,263,934 A | 11/1993 | Haak |
| 5,271,744 A | 12/1993 | Kramer et al. |
| 5,279,543 A | 1/1994 | Glikfeld et al. |
| 5,279,576 A | 1/1994 | Loo et al. |
| 5,279,585 A | 1/1994 | Balkwill |
| 5,279,586 A | 1/1994 | Balkwill |
| 5,281,198 A | 1/1994 | Haber et al. |
| 5,290,228 A | 3/1994 | Uemura et al. |
| 5,295,965 A | 3/1994 | Wilmot |
| 5,300,030 A | 4/1994 | Crossman et al. |
| 5,304,128 A | 4/1994 | Haber et al. |
| 5,304,152 A | 4/1994 | Sams |
| 5,308,341 A | 5/1994 | Chanoch |
| 5,318,522 A | 6/1994 | D'Antonio |
| 5,320,603 A | 6/1994 | Vetter et al. |
| 5,330,431 A | 7/1994 | Herskowitz |
| 5,332,399 A | 7/1994 | Grabenkort et al. |
| 5,334,144 A | 8/1994 | Alchas et al. |
| 5,342,308 A | 8/1994 | Boschetti |
| 5,350,367 A | 9/1994 | Stiehl et al. |
| 5,354,286 A | 10/1994 | Mesa et al. |
| 5,358,489 A | 10/1994 | Wyrick |
| RE34,845 E | 1/1995 | Vetter et al. |
| 5,391,151 A | 2/1995 | Wilmot |
| 5,405,362 A | 4/1995 | Kramer et al. |
| 5,415,648 A | 5/1995 | Malay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,505,694 A | 4/1996 | Hubbard et al. |
| 5,514,097 A | 5/1996 | Knauer |
| 5,514,107 A | 5/1996 | Haber et al. |
| 5,540,664 A | 7/1996 | Wyrick |
| 5,542,760 A | 8/1996 | Chanoch et al. |
| 5,544,234 A | 8/1996 | Terajima et al. |
| 5,549,561 A | 8/1996 | Hjertman |
| 5,554,134 A | 9/1996 | Bonnichsen |
| 5,562,625 A | 10/1996 | Stefancin, Jr. |
| 5,567,160 A | 10/1996 | Massino |
| 5,569,190 A | 10/1996 | D'Antonio |
| 5,569,192 A | 10/1996 | van der Wal |
| 5,569,236 A | 10/1996 | Kriesel |
| 5,573,042 A | 11/1996 | De Haen |
| 5,593,388 A | 1/1997 | Phillips |
| 5,599,302 A | 2/1997 | Lilley et al. |
| 5,599,309 A | 2/1997 | Marshall et al. |
| 5,605,542 A | 2/1997 | Tanaka et al. |
| 5,637,094 A | 6/1997 | Stewart, Jr. et al. |
| 5,637,100 A | 6/1997 | Sudo |
| 5,649,912 A | 7/1997 | Peterson |
| 5,658,259 A | 8/1997 | Pearson et al. |
| 5,665,071 A | 9/1997 | Wyrick |
| 5,688,251 A | 11/1997 | Chanoch |
| 5,695,472 A | 12/1997 | Wyrick |
| 5,704,911 A | 1/1998 | Parsons |
| 5,725,508 A | 3/1998 | Chanoch et al. |
| 5,730,723 A | 3/1998 | Castellano et al. |
| 5,743,889 A | 4/1998 | Sams |
| 5,769,138 A | 6/1998 | Sadowski et al. |
| 5,785,691 A | 7/1998 | Vetter et al. |
| 5,788,670 A | 8/1998 | Reinhard et al. |
| 5,801,057 A | 9/1998 | Smart et al. |
| 5,807,309 A | 9/1998 | Lundquist et al. |
| 5,820,602 A | 10/1998 | Kovelman et al. |
| 5,820,622 A | 10/1998 | Gross et al. |
| 5,827,232 A | 10/1998 | Chanoch et al. |
| 5,836,911 A | 11/1998 | Marzynski et al. |
| 5,843,036 A | 12/1998 | Olive et al. |
| 5,846,233 A | 12/1998 | Lilley et al. |
| 5,851,197 A | 12/1998 | Marano et al. |
| 5,851,198 A | 12/1998 | Castellano et al. |
| 5,860,456 A | 1/1999 | Bydlon et al. |
| 5,865,795 A | 2/1999 | Schiff et al. |
| 5,865,799 A | 2/1999 | Tanaka et al. |
| 5,868,711 A | 2/1999 | Kramer et al. |
| 5,873,857 A | 2/1999 | Kriesel |
| 5,875,976 A | 3/1999 | Nelson et al. |
| 5,879,327 A | 3/1999 | DeFarges et al. |
| 5,891,085 A | 4/1999 | Lilley et al. |
| 5,891,086 A | 4/1999 | Weston |
| 5,893,842 A | 4/1999 | Imbert |
| 5,919,159 A | 7/1999 | Lilley et al. |
| 5,921,966 A | 7/1999 | Bendek et al. |
| 5,925,017 A | 7/1999 | Kriesel et al. |
| 5,928,205 A | 7/1999 | Marshall |
| 5,935,949 A | 8/1999 | White |
| 5,951,528 A | 9/1999 | Parkin |
| 5,957,897 A | 9/1999 | Jeffrey |
| 5,960,797 A | 10/1999 | Kramer et al. |
| 5,989,227 A | 11/1999 | Vetter et al. |
| 6,004,297 A | 12/1999 | Steenfeldt-Jensen et al. |
| 6,045,534 A | 4/2000 | Jacobsen et al. |
| 6,056,716 A | 5/2000 | D'Antonio et al. |
| 6,077,247 A | 6/2000 | Marshall et al. |
| 6,083,201 A | 7/2000 | Skinkle |
| 6,090,070 A | 7/2000 | Hager et al. |
| 6,099,504 A | 8/2000 | Gross et al. |
| 6,123,684 A | 9/2000 | Deboer et al. |
| 6,132,395 A | 10/2000 | Landau et al. |
| 6,159,181 A | 12/2000 | Crossman et al. |
| 6,171,276 B1 * | 1/2001 | Lippe ............... A61M 5/20 128/DIG. 1 |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,221,053 B1 | 4/2001 | Walters et al. |
| 6,223,408 B1 | 5/2001 | Vetter et al. |
| 6,231,540 B1 | 5/2001 | Smedegaard |
| 6,241,709 B1 | 6/2001 | Bechtold et al. |
| 6,245,347 B1 | 6/2001 | Zhang et al. |
| 6,258,078 B1 | 7/2001 | Thilly |
| 6,264,629 B1 | 7/2001 | Landau |
| 6,270,479 B1 | 8/2001 | Bergens et al. |
| 6,309,371 B1 | 10/2001 | Deboer et al. |
| 6,319,224 B1 | 11/2001 | Stout et al. |
| 6,371,939 B2 | 4/2002 | Bergens et al. |
| 6,383,168 B1 | 5/2002 | Landau et al. |
| 6,391,003 B1 | 5/2002 | Lesch, Jr. |
| 6,406,456 B1 | 6/2002 | Slate et al. |
| 6,428,528 B2 | 8/2002 | Sadowski et al. |
| 6,471,669 B2 | 10/2002 | Landau |
| 6,494,865 B1 | 12/2002 | Alchas |
| 6,517,517 B1 | 2/2003 | Farrugia et al. |
| 6,530,904 B1 | 3/2003 | Edwards et al. |
| 6,544,234 B1 | 4/2003 | Gabriel |
| 6,562,006 B1 | 5/2003 | Hjertman et al. |
| 6,565,553 B2 | 5/2003 | Sadowski et al. |
| 6,568,259 B2 | 5/2003 | Saheki et al. |
| 6,569,123 B2 | 5/2003 | Alchas et al. |
| 6,569,143 B2 | 5/2003 | Alchas et al. |
| 6,584,910 B1 | 7/2003 | Plass |
| 6,589,210 B1 | 7/2003 | Rolfe |
| 6,607,508 B2 | 8/2003 | Knauer |
| 6,620,137 B2 | 9/2003 | Kirchhofer et al. |
| 6,641,561 B1 | 11/2003 | Hill et al. |
| 6,645,170 B2 | 11/2003 | Landau |
| 6,656,150 B2 | 12/2003 | Hill et al. |
| 6,673,035 B1 | 1/2004 | Rice et al. |
| 6,682,504 B2 | 1/2004 | Nelson et al. |
| 6,689,092 B2 | 2/2004 | Zierenberg et al. |
| 6,706,000 B2 | 3/2004 | Perez et al. |
| 6,746,429 B2 | 6/2004 | Sadowski et al. |
| 6,767,336 B1 | 7/2004 | Kaplan |
| 6,805,686 B1 | 10/2004 | Fathallah et al. |
| 6,830,560 B1 | 12/2004 | Gross et al. |
| 6,899,698 B2 | 5/2005 | Sams |
| 6,932,793 B2 | 8/2005 | Marshall et al. |
| 6,932,794 B2 | 8/2005 | Giambattista et al. |
| 6,936,032 B1 | 8/2005 | Bush, Jr. et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |

(56) References Cited

U.S. PATENT DOCUMENTS

| | | |
|---|---|---|
| 7,018,364 B2 | 3/2006 | Giambattista et al. |
| 7,066,907 B2 | 6/2006 | Crossman et al. |
| 7,112,187 B2 | 9/2006 | Karlsson |
| 7,118,552 B2 | 10/2006 | Shaw et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,220,247 B2 | 5/2007 | Shaw et al. |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,442,185 B2 | 10/2008 | Amark et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,500,964 B2 | 3/2009 | Shaw et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,635,350 B2 | 12/2009 | Scherer |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Serna et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Abry et al. |
| 2001/0039394 A1 | 11/2001 | Weston |
| 2001/0049496 A1 | 12/2001 | Kirchhofer et al. |
| 2002/0007149 A1 | 1/2002 | Nelson et al. |
| 2002/0045866 A1 | 4/2002 | Sadowski et al. |
| 2002/0173752 A1 | 11/2002 | Polzin |
| 2002/0183690 A1 | 12/2002 | Arnisolle |
| 2002/0188251 A1 | 12/2002 | Staylor et al. |
| 2003/0040697 A1 | 2/2003 | Pass et al. |
| 2003/0083621 A1 | 5/2003 | Shaw et al. |
| 2003/0105430 A1 | 6/2003 | Lavi et al. |
| 2003/0130619 A1 | 7/2003 | Safabash et al. |
| 2003/0158523 A1 | 8/2003 | Hjertman et al. |
| 2003/0171717 A1 | 9/2003 | Farrugia et al. |
| 2003/0229330 A1 | 12/2003 | Hickle |
| 2003/0236502 A1 | 12/2003 | De La Serna et al. |
| 2004/0039336 A1 | 2/2004 | Amark et al. |
| 2004/0039337 A1 | 2/2004 | Letzing |
| 2004/0097783 A1 | 5/2004 | Peters et al. |
| 2004/0097883 A1 | 5/2004 | Roe |
| 2004/0143213 A1 | 7/2004 | Hunter et al. |
| 2004/0220524 A1 | 11/2004 | Sadowski et al. |
| 2004/0267207 A1 | 12/2004 | Veasey et al. |
| 2004/0267355 A1 | 12/2004 | Scott et al. |
| 2005/0020979 A1 | 1/2005 | Westbye et al. |
| 2005/0027255 A1 | 2/2005 | Lavi et al. |

(56) References Cited

U.S. PATENT DOCUMENTS

| | | |
|---|---|---|
| 2005/0033234 A1 | 2/2005 | Sadowski et al. |
| 2005/0080377 A1* | 4/2005 | Sadowski ............ A61M 5/2425 604/131 |
| 2005/0101919 A1 | 5/2005 | Brunnberg |
| 2005/0165360 A1 | 7/2005 | Stamp |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0261634 A1 | 11/2005 | Karlsson |
| 2005/0273054 A1 | 12/2005 | Asch |
| 2006/0025747 A1 | 2/2006 | Sullivan et al. |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2006/0258990 A1 | 11/2006 | Weber |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0088288 A1 | 4/2007 | Barron et al. |
| 2007/0093775 A1 | 4/2007 | Daly |
| 2007/0100288 A1 | 5/2007 | Bozeman et al. |
| 2007/0123818 A1 | 5/2007 | Griffiths et al. |
| 2007/0123829 A1 | 5/2007 | Atterbury et al. |
| 2007/0129686 A1 | 6/2007 | Daily et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0154200 A1 | 6/2008 | Lesch |
| 2008/0185069 A1 | 8/2008 | Clark |
| 2008/0262427 A1 | 10/2008 | Hommann |
| 2008/0262436 A1 | 10/2008 | Olson |
| 2008/0262445 A1 | 10/2008 | Hsu et al. |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0254027 A1 | 10/2009 | Moller |
| 2009/0254035 A1 | 10/2009 | Kohlbrenner et al. |
| 2009/0292240 A1 | 11/2009 | Kramer et al. |
| 2009/0299278 A1 | 12/2009 | Lesch et al. |
| 2009/0304812 A1 | 12/2009 | Staniforth et al. |
| 2009/0312705 A1 | 12/2009 | Grunhut |
| 2009/0318361 A1 | 12/2009 | Noera et al. |
| 2010/0016326 A1 | 1/2010 | Will |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0114058 A1 | 5/2010 | Weitzel et al. |
| 2010/0121272 A1 | 5/2010 | Marshall et al. |
| 2010/0137798 A1 | 6/2010 | Streit et al. |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0191217 A1 | 7/2010 | Hommann et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0258631 A1 | 10/2010 | Rueblinger et al. |
| 2010/0262082 A1 | 10/2010 | Brooks et al. |
| 2010/0262083 A1 | 10/2010 | Grunhut et al. |
| 2010/0268170 A1 | 10/2010 | Carrel et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0292653 A1 | 11/2010 | Maritan |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0034879 A1 | 2/2011 | Crow |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0098656 A1 | 4/2011 | Burnell et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0137247 A1 | 6/2011 | Mesa et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Charles |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0172885 A1 | 7/2012 | Drapeau et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |

(56) References Cited

U.S. PATENT DOCUMENTS

| | | |
|---|---|---|
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |

FOREIGN PATENT DOCUMENTS

| | | |
|---|---|---|
| AU | 2007253481 | 11/2007 |
| AU | 2007301890 | 4/2008 |
| AU | 2008231897 | 10/2008 |
| AU | 2008309660 | 4/2009 |
| AU | 2009217376 | 10/2009 |
| AU | 2009272992 | 1/2010 |
| AU | 2009299888 | 4/2010 |
| AU | 2009326132 | 8/2011 |
| AU | 2009326321 | 8/2011 |
| AU | 2009326322 | 8/2011 |
| AU | 2009326323 | 8/2011 |
| AU | 2009326324 | 8/2011 |
| AU | 2009326325 | 8/2011 |
| AU | 2009341040 | 9/2011 |
| AU | 2010233924 | 11/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010287033 | 4/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2010314315 | 8/2012 |
| AU | 2011212490 | 8/2012 |
| AU | 2011212556 | 8/2012 |
| AU | 2011212558 | 8/2012 |
| AU | 2011212561 | 8/2012 |
| AU | 2011212564 | 8/2012 |
| AU | 2011212566 | 8/2012 |
| AU | 2011212567 | 8/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011270934 | 1/2013 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 2473371 | 7/2003 |
| CA | 2557897 | 10/2005 |
| CA | 02702412 | 12/2008 |
| CN | 101094700 | 12/2007 |
| CN | 101128231 | 2/2008 |
| CN | 101184520 | 5/2008 |
| CN | 101400394 | 4/2009 |
| CN | 101405582 | 4/2009 |

(56) References Cited

FOREIGN PATENT DOCUMENTS

| | | |
|---|---|---|
| CN | 101479000 | 7/2009 |
| CN | 101511410 | 8/2009 |
| CN | 101516421 | 8/2009 |
| CN | 101557849 | 10/2009 |
| CN | 101563123 | 10/2009 |
| CN | 101563124 | 10/2009 |
| CN | 101594898 | 12/2009 |
| CN | 101600468 | 12/2009 |
| CN | 101605569 | 12/2009 |
| CN | 101610804 | 12/2009 |
| CN | 101626796 | 1/2010 |
| CN | 101678166 | 3/2010 |
| CN | 101678172 | 3/2010 |
| CN | 101678173 | 3/2010 |
| CN | 101687078 | 3/2010 |
| CN | 101687079 | 3/2010 |
| CN | 101687080 | 3/2010 |
| CN | 101715371 | 5/2010 |
| CN | 101909673 | 12/2010 |
| CN | 101912650 | 12/2010 |
| CN | 101939034 | 1/2011 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102639170 | 8/2012 |
| CN | 102639171 | 8/2012 |
| CN | 102648014 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102695531 | 9/2012 |
| CN | 102695532 | 9/2012 |
| CN | 102711878 | 10/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| CN | 102895718 | 1/2013 |
| CN | 102905613 | 1/2013 |
| CN | 102905742 | 1/2013 |
| CN | 102905743 | 1/2013 |
| CN | 102905744 | 1/2013 |
| CN | 102905745 | 1/2013 |
| CN | 102917738 | 2/2013 |
| CN | 102917743 | 2/2013 |
| DE | 102006041809 | 3/2008 |
| DE | 202011110155 | 12/2012 |
| DK | 1646844 | 12/2009 |
| DK | 2229201 | 7/2012 |
| DK | 2023982 | 10/2012 |
| DK | 2274032 | 10/2012 |
| DK | 02346552 | 11/2012 |
| DK | 1888148 | 1/2013 |
| DK | 2288400 | 1/2013 |
| DK | 2373361 | 1/2013 |
| DK | 1885414 | 2/2013 |
| DK | 2174682 | 2/2013 |
| DK | 2310073 | 2/2013 |
| EG | 25844 | 9/2012 |
| EP | 0072057 | 2/1983 |
| EP | 0103664 | 3/1984 |
| EP | 1752174 | 3/1986 |
| EP | 245895 | 11/1987 |
| EP | 255044 | 2/1988 |
| EP | 361668 | 4/1990 |
| EP | 0518416 | 12/1992 |
| EP | 525525 | 2/1993 |
| EP | 1067823 | 1/2001 |
| EP | 1161961 | 12/2001 |
| EP | 1307012 | 5/2003 |
| EP | 1518575 | 3/2005 |
| EP | 1140260 | 8/2005 |
| EP | 1944050 | 7/2008 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| ES | 2394556 | 2/2013 |
| FR | 2506161 | 11/1982 |
| FR | 2635009 | 2/1990 |
| GB | 6677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | 10-507935 | 8/1998 |
| JP | 11-347121 | 12/1999 |
| JP | 2000-245839 | 9/2000 |
| JP | 2001-523485 | 11/2001 |
| JP | 5016490 | 5/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 4970282 | 7/2012 |
| JP | 4970286 | 7/2012 |
| JP | 4972147 | 7/2012 |
| JP | 4977209 | 7/2012 |
| JP | 4977252 | 7/2012 |
| JP | 4979686 | 7/2012 |
| JP | 4982722 | 7/2012 |
| JP | 2012515566 | 7/2012 |
| JP | 2012515585 | 7/2012 |
| JP | 2012515587 | 7/2012 |
| JP | 2012516168 | 7/2012 |
| JP | 2012516736 | 7/2012 |
| JP | 2012516737 | 7/2012 |
| JP | 4990151 | 8/2012 |

(56) References Cited

FOREIGN PATENT DOCUMENTS

| | | |
|---|---|---|
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012519508 | 8/2012 |
| JP | 2012519511 | 8/2012 |
| JP | 2012519514 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| JP | 5084825 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120091009 | 8/2012 |
| KR | 20120091153 | 8/2012 |
| KR | 20120091154 | 8/2012 |
| KR | 20120095919 | 8/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| MX | 2012006694 | 7/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 88/08724 | 11/1988 |
| WO | WO 91/13299 | 9/1991 |
| WO | WO 91/13430 | 9/1991 |
| WO | WO 92/19296 | 11/1992 |
| WO | WO 94/09839 | 5/1994 |
| WO | WO 94/11041 | 5/1994 |
| WO | WO 95/29720 | 11/1995 |
| WO | WO 95/29730 | 11/1995 |
| WO | WO 96/21482 | 7/1996 |
| WO | WO 97/14455 | 4/1997 |
| WO | WO 97/21457 | 6/1997 |
| WO | WO 97/41907 | 11/1997 |
| WO | WO 97/48430 | 12/1997 |
| WO | WO 98/31369 | 7/1998 |
| WO | WO 98/32451 | 7/1998 |
| WO | WO 9831369 | 7/1998 |
| WO | WO 9832451 | 7/1998 |
| WO | WO 99/03521 | 1/1999 |
| WO | WO 99/10030 | 3/1999 |
| WO | WO 99/22790 | 5/1999 |
| WO | WO 9922789 | 5/1999 |
| WO | WO 99/62525 | 12/1999 |
| WO | WO 9962525 | 12/1999 |
| WO | WO 0006228 | 2/2000 |
| WO | WO 00/24441 | 5/2000 |
| WO | WO 00/29050 | 5/2000 |
| WO | WO 01/93926 | 12/2001 |
| WO | WO 02/083216 | 10/2002 |
| WO | WO 02/089805 | 11/2002 |
| WO | WO 02089805 | 11/2002 |
| WO | WO 03047663 | 6/2003 |
| WO | WO 03/070296 | 8/2003 |
| WO | WO 03068290 | 8/2003 |
| WO | WO 03070296 | 8/2003 |
| WO | WO 03/097133 | 11/2003 |
| WO | WO 03097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/002653 | 1/2005 |
| WO | WO 2005/005929 | 1/2005 |
| WO | WO 2005/009515 | 2/2005 |
| WO | WO 2005/053778 | 6/2005 |
| WO | WO 2006/079064 | 7/2006 |
| WO | WO 2006/086899 | 8/2006 |
| WO | WO 2006/125328 | 11/2006 |
| WO | WO 2006/130098 | 12/2006 |
| WO | WO 2007/047200 | 4/2007 |
| WO | WO 2007/063342 | 6/2007 |
| WO | WO 2007/100899 | 9/2007 |
| WO | WO 2007/104636 | 9/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/089886 | 7/2008 |
| WO | WO 2008/100576 | 8/2008 |

(56) References Cited

FOREIGN PATENT DOCUMENTS

| | | |
|---|---|---|
| WO | WO 2008/107378 | 9/2008 |
| WO | WO 2008/112472 | 9/2008 |
| WO | WO 2009049885 | 4/2009 |
| WO | WO 2008/071804 | 8/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/042537 | 4/2011 |
| WO | WO 2011/042540 | 4/2011 |
| WO | WO 2011/043714 | 4/2011 |
| WO | WO 2011/045385 | 4/2011 |
| WO | WO 2011/045386 | 4/2011 |
| WO | WO 2011/045611 | 4/2011 |
| WO | WO 2011/046756 | 4/2011 |
| WO | WO 2011/048223 | 4/2011 |
| WO | WO 2011/048422 | 4/2011 |
| WO | WO 2011/050359 | 4/2011 |
| WO | WO 2011/051366 | 5/2011 |
| WO | WO 2011/053225 | 5/2011 |
| WO | WO 2011/054648 | 5/2011 |
| WO | WO 2011/054775 | 5/2011 |
| WO | WO 2011/056127 | 5/2011 |
| WO | WO 2011/060087 | 5/2011 |
| WO | WO 2011/067187 | 6/2011 |
| WO | WO 2011/067268 | 6/2011 |
| WO | WO 2011/067320 | 6/2011 |
| WO | WO 2011/067615 | 6/2011 |
| WO | WO 2011/068253 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | WO 2011/107805 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2011/117404 | 9/2011 |
| WO | WO 2011/121003 | 10/2011 |
| WO | WO 2011/121061 | 10/2011 |
| WO | WO 2011/123024 | 10/2011 |
| WO | WO 2011/124634 | 10/2011 |
| WO | WO 2011/126439 | 10/2011 |
| WO | WO 2012020084 | 2/2012 |
| WO | WO 2012022771 | 2/2012 |
| WO | WO 2012/090186 | 7/2012 |
| WO | WO 2012/122643 | 9/2012 |

OTHER PUBLICATIONS

International Patent Application No. PCT/US14/23485, International Search Report, dated Jul. 7, 2014, 2 pages.
International Patent Application No. PCT/US14/24530, International Search Report, dated Jul. 15, 2014, 2 pages.
International Patent Application No. PCT/US14/24543, International Search Report, dated Jul. 28, 2014, 2 pages.
"Skin", American Medical Association (AMA) Current Procedural Terminology , 1998, http://www.ama-assn.org/ama/pub/category/print/7176.html, 1 page.
Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1), pp. 73-81.
Chen et al., "Blood Lipid Profiles and Peripheral Blood Mononuclear Cell Cholesterol Metabolism Gene Expression in Patients with and Without Methotrexate" BMC Medicine, 2011, 9(4), 9 pages.
Chiasson et al., "Continuous Subcutaneous Insulin Infusion (Mill-Hill Infuser) Versus Multiple Injections (Medi-Jector) in the Treatment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with Communication dated Apr. 25, 2005 regarding Proceeding Further with the European Patent Application Pursuant to Article 96(1), and Rule 51(1) EPC, 3 pages.

(56) References Cited

OTHER PUBLICATIONS

European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31(6), pp. 361-366.
Hoekstra et al., Bioavailability of Higher Dose Methotrexate Comparing Oral and Subcutaneous Administration i n Patients with Rheumatoid Arthritis, The Journal of Rheumatology, 2004, 31(4), pp. 645-648.
International Patent Application No. PCT/US2012/46742, International Search Report and Written Opinion dated Nov. 16, 2012, 11 pages.
International Patent Application No. PCT/US2009/052835, International Search Report dated Mar. 15, 2010, 5 pages.
International Patent Application No. PCT/US2013/029085, International Search Report dated May 13, 2013, 2 pages.
International Patent Application No. PCT/US2010/028011, International Search Report, dated Jun. 29, 2010, 5 pages.
International Patent Application No. PCT/US2009/036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes Care, Nov.-Dec. 1986, 9(6), 637-640.
"The Historical Development of Jet Injection and Envisioned Uses in Mass Immunization and Mass Therapy Based Upon Two Decades' Experience", Military Medicine, Jun. 1963, 128, pp. 516-524.
Pehling et al, "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US2013/029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.
Tukova et al., "Methotrexate Bioavailability after Oral and Subcutaneous Administration in Children with Juvenile Idiopathic Arthritis", Clinical and Experimental Rheumatology, 2009, 27, 1047-1053.
Wright et al., "Stability of Methotrexate Injection in Prefilled Plastic Disposable Syringes", International Journal of Pharmaceutics, Aug. 1988, 45(3), 237-244.
Lunenfeld, "Stable Testosterone Levels Achieved with Subcutaneous Testosterone Injections", The aging Male, Mar. 2006, 9(1), 70 pages.

\* cited by examiner

TWO-STAGE RECONSTITUTING INJECTOR

CROSS-REFERENCE TO RELATED APPLICATIONS

The present application is continuation of and claims priority benefit of U.S. Non-Provisional patent application Ser. No. 13/584,317, filed on 13 Aug. 2012, now allowed, which in turn is a continuation of U.S. Non-Provisional patent application Ser. No. 12/299,274, filed 2 May 2007, now issued as U.S. Pat. No. 8,251,947, which in turn is a U.S. National Stage Entry of PCT/US2007/067986, filed 2 May 2007, which in turn claims priority benefit from U.S. Provisional Patent Application No. 60/796,939, filed 3 May 2006, all of which are hereby incorporated by reference in their entireties.

FIELD OF THE INVENTION

The present invention relates to an injector, and more particularly to an injector in which materials from at least two compartments are contained before the injection is made.

BACKGROUND OF THE PRESENT INVENTION

Known injection devices for injection of medicaments into a patient include traditional hypodermic needle syringes, needle-free jet injectors like the ones disclosed in U.S. Pat. Nos. 5,599,302; 5,062,830; and 4,790,824; needle-assisted injectors, such as those described in U.S. Patent Publication No. 2005/0033234; and self-injectors or auto-injectors like the ones disclosed in U.S. Pat. Nos. 4,553,962 and 4,378,015, and PCT Publications WO 95/29720 and WO 97/14455.

The liquid medicament preparations that are injected from such injection devices are also known to contain insoluble or particulate drug constituents. This can be due to the insolubility of the drug in the vehicle or medium in which it is stored. As a result, the insoluble or particulate drug constituents in the liquid preparations separate upon storage, even over short periods of time.

The particulates can potentially clog the needle, and this is particularly problematic in cases when the liquid pharmaceutical preparation containing insoluble particles is self-administered or administered in the home by non-professional care-givers. Ordinarily, when these liquid pharmaceutical preparations are administered in the hospital or other health-care providing institutions by trained staff, one can rely on adequate handling of the medication to ensure proper drug delivery, despite settled material and plugged needles. However when such pharmaceutical preparations are self-administered or administered in the home by non-professional care-givers, the risk for inadequate handling of the medication increases since the injection of such formulations requires that the administrator be able to adequately resuspend any settled material and clear the needle to ensure proper drug delivery.

Thus, an injector is needed that can facilitate reliable combination of injectable components prior to injection.

SUMMARY OF THE INVENTION

The invention is related to an injector for injecting a medicament into a patient. The preferred embodiment of the injector includes a container defining a first chamber containing a fluid therein, and a second chamber. An injection conduit is configured for directing the fluid fired from the container into the patient. The injector also includes a transfer mechanism operable by a user to transfer the fluid from the first chamber to the second chamber in a first stage of operation, and a firing mechanism operable by the user for firing the fluid from the second chamber through the injection conduit in a second stage of operation. An energy source is in powering association with the firing mechanism to drive firing mechanism in the first and second stages.

Preferably, the injector also includes a transfer control that is manually operable to operate the injector in the first stage of operation. The first stage preferably also includes venting the second chamber. The injection conduit preferably has a position that is initially fluidly incommunicated with the second chamber, and the transfer control preferably operates the transfer mechanism in the first stage of operation and fluidly communicates the injection conduit with the second chamber in the first stage of operation. Preferably, the transfer control includes a cap associated with the container and disposed to cover the injection conduit prior to the first stage of operation. Also, the cap is preferably separable from the injection conduit and container after the first stage of operation. Preferably, the injector includes a cap release in locking association with the cap to prevent operation thereof. The cap release is positionable in a release position in which the cap release releases the cap to permit operation thereof in the first stage of operation.

The injection conduit preferably includes a communicating needle portion, and the transfer control is operable to relatively move the communicating needle portion with respect to the second chamber to pierce the container to fluidly communicate the second chamber with the communicating needle portion in the first stage of operation. The injection conduit also preferably includes an injecting needle portion disposed and configured to pierce the skin of the patient for assisting the injection of the fluid in the second stage.

Preferably, the energy source and firing mechanism are configured for delivering the fluid in a jet to an injection site within the patient tissue remote from the injecting needle. The injection conduit preferably includes a jet nozzle disposed and configured to deliver the fluid in a jet into the patient during the second stage of operation to pierce the skin of the patient for assisting the injection of the fluid in the second stage.

Preferably, the second chamber comprises the medicament, and the fluid in the first chamber is a diluent configured for dissolving or suspending the medicament therein for injection into the patient. The energy source is preferably associated to power the transfer mechanism to transfer the fluid to the second chamber. The preferred injector also includes an injection trigger mechanism operably associated with the firing mechanism to operate the firing mechanism in the second stage. The transfer and firing mechanisms can include a firing ram that is movable over a first throw in the first stage of operation and a second throw in the second stage of operation, the energy source in biasing association with the ram in each stage of operation to power the ram. The injection trigger mechanism is configured to block movement of the ram beyond the first throw, the injection trigger being acuatable to release the ram to travel over the second throw.

The injector also preferably includes a retractable guard that is movable between a protecting position in which the injection conduit is disposed within the guard, and an injecting position in which an injection needle portion of the injection conduit is exposed for injection of the fluid in the patient. Preferably, the injection trigger mechanism is configured for operating the firing mechanism in the second stage after the retractable guard is retracted from the protecting position. Also, the retractable guard can be operably associated with the injection trigger mechanism to cause the injection trigger mechanism to operate the firing mechanism when the guard is retracted to the injecting position.

In another preferred embodiment, the injector includes a container that includes a fluid chamber containing a medicament therein, the fluid chamber comprising a needle hub at the distal end thereof, and an injection conduit configured for directing the medicament fired from the container into the patient, the injection conduit having a position that is fluidly incommunicated with the fluid chamber. The injector also includes a transfer control operable to fluidly communicate the injection conduit with the needle hub of the fluid chamber. The transfer control includes a cap associated with the container and disposed to cover the injection conduit, the cap being separable from the injection conduit upon operating the transfer control to fluidly communicate the injection conduit with the needle hub.

Preferably, the injection conduit includes a communicating needle portion, the transfer control being operable to relatively move the communicating needle portion with respect to the fluid chamber to pierce the container adjacent the needle hub to fluidly communicate the fluid chamber with the communicating needle portion.

A trigger device can be associated with the energy source and the firing mechanism, with the triggering device being operable in a first triggering stage, which causes the firing mechanism to operate in the first stage of operation. The triggering device can be configured such that only after the firing mechanism has operated in the first stage of operation, the triggering device is operable in a second triggering stage which causes the firing mechanism to operate in the second stage of operation. The triggering device can have a single control that is operable in the first and second triggering stages, or separate controls to operate in each of the first and second triggering stages.

The present invention thus provides an injector that enables reconstitution of a liquid medicament preparation, preferably just prior to injection, to enable easy and effective delivery of the medicament to a patient.

BRIEF DESCRIPTION OF THE DRAWINGS

FIG. 3 is a side view of a flex arm, flex arm cam, and an outer sleeve arm of the injector of FIG. 1;

DETAILED DESCRIPTION OF THE PREFERRED EMBODIMENTS

Figure 1:
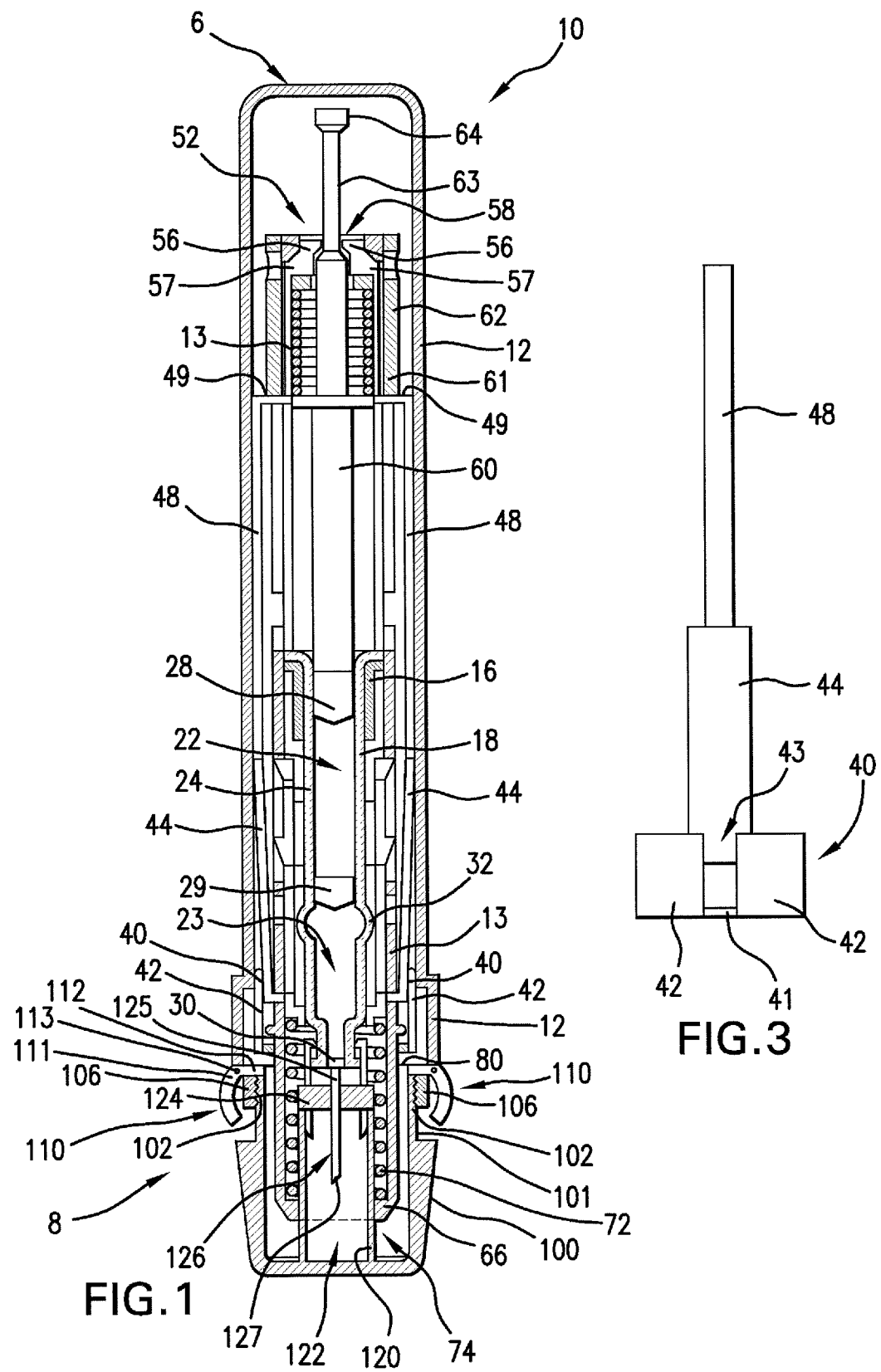
FIG. 1 is a cross-sectional view of a preferred embodiment of an injector constructed according to the present invention, showing the injector with a cap associated therewith.

Referring to FIG. 1, a preferred embodiment of an injector 10 has a tubular outer housing 12 having a proximal end 6 and a distal end 8, and configured for allowing a user to handle the injector 10 and position the injector near or adjacent an injection location of a patient. The outer housing 12 preferably houses most of the components of the injector 10.

Figure 2:
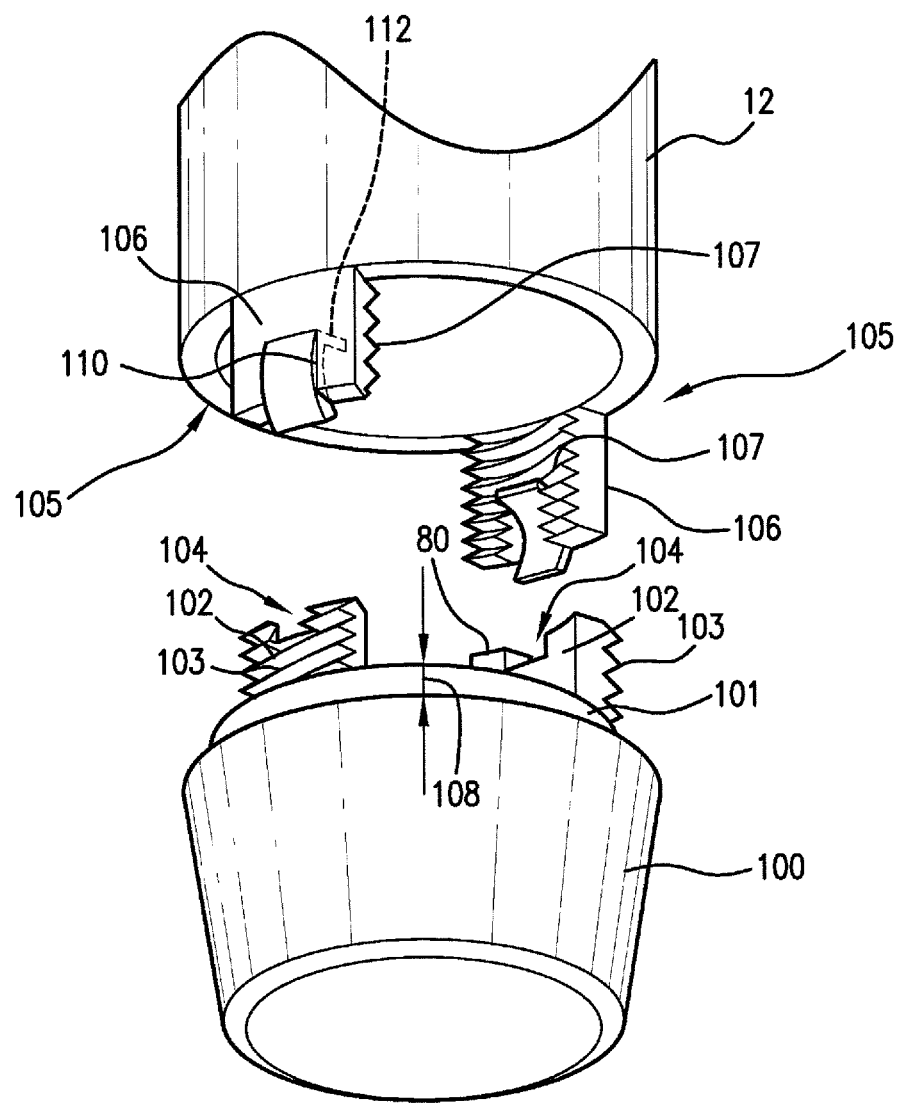
FIG. 2 is a perspective view of the distal end of the housing thereof, with the cap removed.

A cap 100 is associated with the outer housing 12 at the distal end 8 and is configured for covering an injection conduit, which can be a needle 126, or a jet nozzle, for example. The cap 100 preferably includes engagement portions configured for removable engagement with outer housing 12. As shown in the preferred embodiment of FIGS. 1 and 2, the cap 100 preferably includes a radially recessed neck 101 extending a distance 108 from the proximal end thereof. The neck 101 preferably has a smaller diameter than the remaining portion of the cap 100, but can have the same or larger diameter in other embodiments. A pair of engagement portions 102 extend preferably proximally towards the outer housing 12 from the neck 101, such as on opposing sides there. Each of the engagement portions 102 preferably extends circumferentially around less than about a quarter, and more preferably less than about a fifth, of the total circumference of the neck 101. The outer radial surface of the engagement portions 102 is preferably a threaded surface 103 configured for threadably associating with a portion of the outer housing 12. The engagement portions 102 also preferably include a notch 104 at the proximal end thereof and which is configured for associating with another portion of the outer housing 12.

The distal end of the outer housing 12 also preferably includes engagement portions 106 configured for removable engagement with the cap 100. Engagement portions 106 extend distally from positions to engage the cap engagement portions 102, and in this embodiment are disposed diametrically opposite sides of the distal end 8 of the outer housing 12. Similar to the engagement portions 102 of the cap 100, the engagement portions 106 of the outer housing 12 preferably extend circumferentially around less than about a quarter, and more preferably less than about a fifth, of the total circumference of the distal end 8 of the outer housing 12. The inner radial surface of the engagement portions 106 is preferably a threaded surface 107. Additionally, the engagement portions 106 preferably define a pair of gaps 105 therebetween, the circumferential length of the gaps 105 preferably larger than the circumferential length of the engagement portions 102 of the cap 100.

Preferably, the width between circumferentially adjacent engagement portions 106 of the outer housing 12 is greater than the width between engagement portions 102 of the cap 100, such that when the cap 100 and outer housing 12 are engaged with each other as shown in FIG. 1, the threaded surface 103 of the engagement portions 102 are in threaded association with the threaded surface 107 of the engagement portions 106, with the engagement portions 102 disposed radially inward with respect to the engagement portions 106.

One or both of the engagement portions 106 preferably further includes a cap lock mechanism 110 that is moveable between a blocking position and a release position. The cap lock mechanism 110 includes an actuation portion 111 that is operable by the user, a blocking portion 112, and a pivot 113 that is mounted preferably to the outer housing 12. When the engagement portions 102 and 106 are in threaded association with each other such that the cap 100 and the outer housing 12 are engaged, each cap lock mechanism 110 is resiliently biased to the blocking position such that each blocking portion 112 is disposed within respective notches 104. In this position, the blocking portion 112 prevents rotation of the cap 100 with respect to the outer housing 12, at least in a direction that would allow cap release, and preferably in both directions. Movement of the cap 100 in the proximal direction with respect to the outer housing 12 is also thus prevented. Actuation of the cap lock mechanism 110, for example, by depressing the actuation portion 111 radially inward, causes the blocking portion 112 to pivot proximally about pivot 113 to a release position. As a result, the blocking member 112 pivots out of association with the notch 104 to a position in which rotation in a cap release direction is permitted, and no longer prevents or obstructs movement of the cap 100 in the proximal direction with respect to the outer housing 12. Preferably, the actuation portion 111 is a button, although it can be any other suitable actuation member in other embodiments, and alternative mechanisms can be used to lock the cap in a protective position. In other embodiments, the cap lock mechanism can be mounted on the cap and be disengageable with notches located on the engagement portions of the outer housing.

The interior of the cap 100 preferably includes a hub-engagement portion 120, which is preferably substantially annular, that defines a holding area 122 therein. The hub-engagement portion 120 is preferably configured for reception in axial opening 74 of guard 66 of the injector 10. Releasably mounted within the holding area 122 is a needle hub 124 to which an injection needle 126, or other injection conduit, is mounted. In a needle-free embodiment, a jet nozzle can be mounted thereto. The needle hub 124 preferably is in a snap-lock association with the holding area 122 of the cap 100, but alternatively can be abutting the cap for free removal therefrom. The needle 126 preferably includes a piercing end 125 and an injection end 127 that terminates in an injection tip. The injection end 127 is preferably configured as known in the art to penetrate the tissue of a patient, preferably the skin, at the injection location. A needle bore extends through the needle 126 forming a conduit for the medicament. Preferably, the needle hub 124 is attached to the needle 126 so that the piercing end 125 is oriented proximally, and the injection end 127 is oriented distally, with respect to the outer housing 12.

In other embodiments, the cap and distal end of the housing can have different configurations for allowing removable engagement therebetween. For example, the cap and housing can include associable bayonet fittings, latch fittings, snap fittings, or other suitable attachment structures.

The injector 10 also includes container support member 16 housed within and mounted with the inner housing 13. The container support member 16 is configured to hold and position a container within the injector 10. The container can be, for example, a cartridge 18 or any other suitable container for holding medicament therein. In the preferred embodiment, the container support member 16 is substantially fixed to the inner housing 13, such as by snaps, an adhesive, a weld, or another known attachment, but may be mounted therein in other manners.

The cartridge 18 preferably includes a container portion 24 that defines in its interior a diluent chamber 22, which is preferably prefilled with a liquid diluent, and a medicament or drug chamber 23, which is preferably prefilled with a particulate drug. The container portion 24 is preferably tubular or cylindrical in shape. The diluent chamber 22 is preferably aligned with and disposed proximally with respect to the medicament chamber 23. Additionally, the diluent chamber 22 is defined by a first plunger 28 at the proximal end of the chamber, a second plunger 29 at the distal end of the chamber, and by the wall of the container portion 24. Similarly, the medicament chamber 23 is defined by the second plunger 29 at the proximal end of the chamber, a membrane, septum 30, or stopper at the distal end of the chamber, and by the wall of the container portion 24. The distal end of the medicament chamber 23, adjacent the septum 30, is preferably configured for engagement and mounting of the needle hub 124 therewith.

A preferred material for the container portion 24 is glass, for example, borosilicate glass that is compatible with most medicaments, but other suitable materials can be used in other embodiments. The first and second plungers or stoppers 28, 29, and the septum 30 seal the respective contents of diluent chamber 22 and medicament chamber 23 therein.

The container 18 also preferably includes a by-pass or a reconstitution bulge 32 where the walls of the container are flared radially outward along a longitudinal length thereof. As such, the radial diameter of the reconstitution bulge 32 is preferably substantially larger than the remaining portions of the container 18. Preferably, the radial diameter and the longitudinal length of the reconstitution bulge 32 is also substantially larger than that of the second plunger 29. The reconstitution bulge 32 is preferably located within the medicament chamber 23 before the injection is commenced or the contents of the diluent and medicament chambers are combined.

The injector 10 also preferably includes a flex arm cam member 40, flex arms 44, and ram arms 48 contained within the outer housing 12, as shown in FIG. 1. FIG. 3 shows a side view of the relationship between such components. The flex arm cam member 40 is preferably disposed near the distal end of the outer housing 12 such that base 41 of the flex arm cam member 40 is proximally adjacent the cap 100. The flex arm cam member 40 also includes flex arm cams 42 that extend proximally from the base 41 to adjacent a distal portion of one of the flex arms 44. The flex arm cams 42 also define a slot 43 therebetween configured for receiving a portion of the ram arm 48.

The distal end of the of the flex arm 44 can be mounted to inner housing 13 or another suitable portion of the injector 10. The distal portion of the flex arms 44 are disposed radially inward with respect to the flex arm cams 42. The flex arms 44 extend proximally from the flex arm cams 42. The flex arms 44 are shown in a blocking position in FIG. 1. The flex arms 44 are preferably made of a resilient, flexible material such that the proximal ends of the flex arms 40 can flex radially inward upon application of a force thereto to assume a release position.

In the blocking position, the proximal ends of each flex arm 44 is disposed in longitudinal abutment with, and preferably in substantial longitudinal alignment with, the distal end of a respective ram arm 48. The ram arms 48 further extend proximally therefrom to respective shoulders 49, which extend radially inward from each ram arm 48. Preferably, the shoulder 49 is attached to ram 60, which is associated with and biased by an energy source, which in the embodiment of FIG. 1 is a compression spring 62, although other suitable energy sources can alternatively be used such as elastomer, compressed-gas springs, or gas generators. A preferred type of compression spring is a coil spring. As a result, the ram arms 48 are also biased distally by the spring 62, and thus the distal end of each ram arm 48 is biased against the proximal end of each flex arm 44 when the flex arms are in the blocking position. The distal end of the ram 60 is disposed adjacent the proximal end of the first plunger 28. Although the ram 60 is biased distally against the first plunger 28 by the spring 62, the ram 60 is prevented from displacing the first plunger 28 because the ram arms 48 are blocked by the flex arms 44.

The ram 60 also includes a proximal portion that includes a shaft 63 and terminates proximally at enlarged portion or end 64. The enlarged end 64 preferably has a radial diameter that is substantially greater than that of the shaft 63, and which is also too large to fit through aperture 58 between the trigger protrusions 56, which thus prevents or impedes distal movement of the ram 60 past where the trigger protrusions 56 would abut the enlarged end 64.

Figure 4:
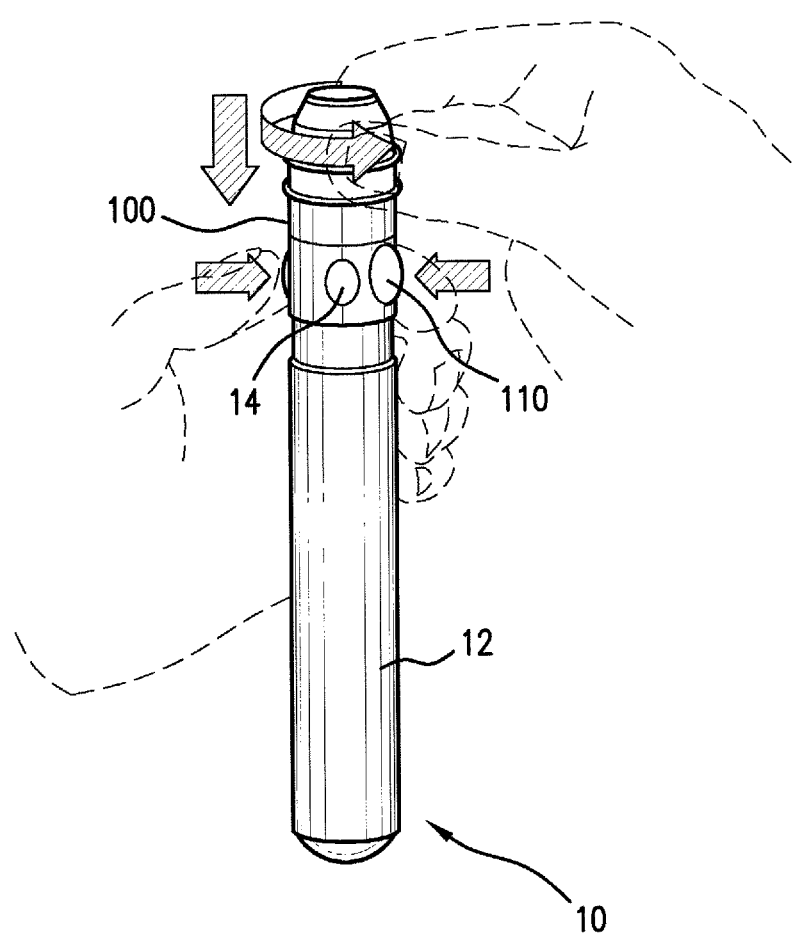
FIG. 4 is a perspective view of another embodiment of an injector device with the cap being removed.

The features of the injector 10 as described above advantageously allow the injector 10 to complete a first stage of operation, which effectively prepares the medicament and readies the injector 10 for injection. Prior to commencement of the first stage of operation, the injector 10 is preferably oriented such that the cap 100, which is in threaded association with the outer housing 12, is above the rest of the injector 10, as shown in FIG. 4. In some embodiments, a safety wrapping is affixed to the cap and the housing, the removal of which is required in order to commence the first stage of operation. Additionally, the safety wrapping can include indicia thereon to indicate that the injector should be oriented with the cap above the rest of the injector prior to commencing the first stage of operation, as well as other instructions.

In the preferred embodiment, the first stage of operation is initiated by actuation or depression of the cap lock mechanisms 110 to enable the cap 100 to be unlocked from fixed engagement with the outer housing 12. Upon actuation of the cap lock mechanisms 110, the blocking portions 112 are pivoted proximally about the pivot 113 to the release position, and thus the cap 100 is free to rotate. Upon rotation of the threads, the cap 100 moves proximally with respect to the outer housing 112, as shown in FIG. 4. Preferably, the cap 100 is able to simultaneously rotate and move proximally. Instead of threads, alternative embodiments can use other mechanisms, such as modified bayonet fittings of the cap to the housing, or by a cam mechanism. The cap 100 is preferably able to move proximally with respect to the outer housing 12 until a proximal portion of the cap 100 contacts the distal end of the engagement portions 106, which can act to limit proximal movement of the cap 100. Preferably, a quarter-turn rotation of the cap 100 is sufficient to move the cap to actuate the first stage mechanism or transfer mechanism, which in this embodiment includes cap 100, flex arm cam member 40, flex arms 44, and ram arms 48, and also to completely disengage the respective threaded surfaces 103, 107 of the engagement portions 102, 106 from threaded association with each other (e.g., rotating the cap so as to dispose the engagement portions 102 within the gaps 105 defined between the engagement portions 106, or vice versa). In other embodiments, the cap and housing can be configured to require rotation of the cap first until disengagement of the engagement portions, subsequently followed by movement of the cap proximally relative to the housing.

Figure 5:
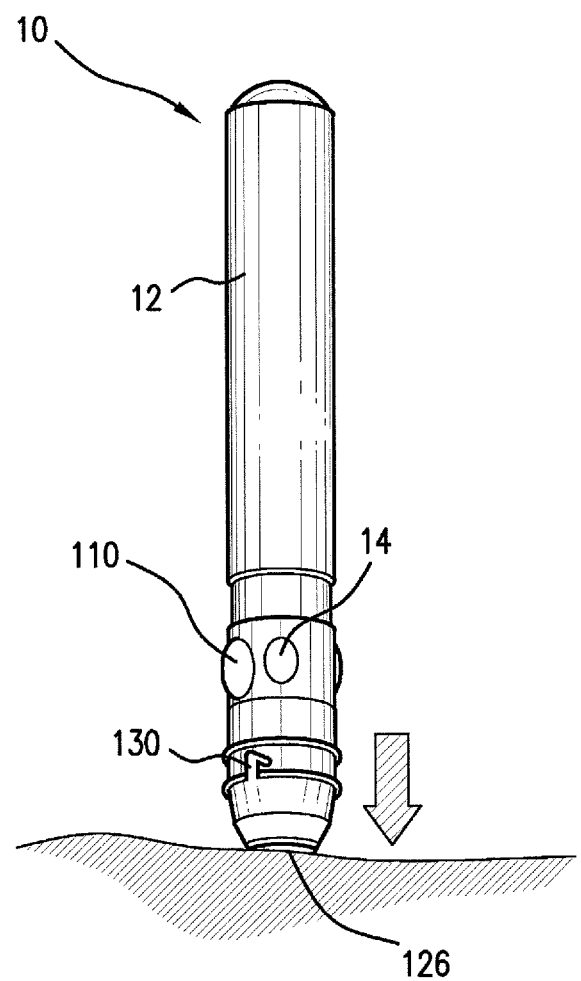
FIG. 5 is a perspective view thereof during injection.

In another embodiment, as shown in FIG. 5 for example, engagement between the cap and the outer housing is directed by a modified bayonet fitting 130 disposed on the outer housing 12. The fitting 130 includes a longitudinal slot and a lateral slot, and the cap preferably includes a cap protrusion configured to slide within the longitudinal and lateral slots. In this configuration, the cap protrusion is located at the end of the lateral slot when the cap and outer housing are engaged, and disengagement is preferably achieved by rotation of the cap such that the cap slides along the lateral slot, followed by longitudinal movement of the cap away from the outer housing such that the cap slides along the longitudinal slot to separate the cap therefrom.

In the preferred embodiment, rotation of the cap 100 with respect to the outer housing 12 disengages the engagement portions 102, 106 from threaded association with each other, thus allowing the cap 100 to be completely removed from association with the outer housing 12 by pulling the cap 100 distally away therefrom. Prior to such removal of the cap, however, movement of the cap 100 proximally with respect to the outer housing 12 also preferably initiates the first stage of operation, which preferably includes attaching the injection conduit in fluid communication with the medicament chamber 23.

For example, movement of the cap 100 in the proximal direction also moves the needle hub 124 proximally such that the needle hub 124 is received on the distal end of the medicament chamber 23 and securely mounted thereto. Preferably, the needle hub 124 has a snap-lock association with the distal end of the medicament chamber 23 that is of greater strength than the snap-lock association between the needle hub 124 and the holding area 122. Thus, the needle hub 124 will remain mounted to the distal end of the medicament chamber 23 even after removal of the cap 100 from the injector 10 by pulling the cap distally.

Additionally, upon moving the needle hub 124 proximally for mounting, the piercing end 125 of the needle 126 preferably pierces or punctures the septum 30 at the distal end of the medicament chamber 23. This puts the bore of the needle 126 in fluid communication with the medicament chamber 23 and the medicament therein, and is open at the needle tip 127 to inject the medicament therethrough. The fluid communication between the needle 126 and the medicament chamber 23 also acts to vent the chamber, thus allowing air within the chamber to escape or be released through the bore of the needle 126, such as upon movement of the plungers 28, 29 through the diluent and medicament chambers 22, 23. Orientation of the injector 10 with the cap 100 above the injector 10 advantageously facilitates efficient venting of the medicament chamber 23, without the medicament leaking from the needle hub 124.

Movement of the cap 100 in the proximal direction also causes a proximal side 80 of cap 100 to contact and push the base 41 of the flex arm cam member 40. Upon engagement by the proximal side 80, the flex arm cam member 40 is also moved in the proximal direction, sliding the flex arm cams 42 proximally along and against the distal portions of the flex arms 44. The flex arm cams 42 thus cam the flexible flex arms 44 radially inwardly from the blocking position to the release position with respect to the ram arms 48. Because the flex arms 44 in the release position are no longer longitudinally aligned with the ram arms 48, the spring 62 is able to move the ram 60 in the distal direction until the enlarged end 64 reaches aperture 58, where the trigger protrusions 56 prevent further distal movement of the ram 60. In the first stage operation, the ram 60 preferably moves longitudinally by a predetermined first amount, which is less than full travel. As the ram 60 moves distally, the ram arms 48 also slide distally radially over the flex arms 44, and the distal portions of the ram arms 48 are received within slots 43 between the flex arm cams 42.

Movement of the ram 60 distally also moves the first plunger 28 in the distal direction, pushing the diluent in the diluent chamber 22, which pushes the second plunger 29 in the distal direction until second plunger 29 reaches the reconstitution bulge 32. When the second plunger 29 enters the reconstitution bulge 32, a fluid passageway is created between the diluent chamber 22 and the medicament chamber 23, allowing diluent from the diluent chamber 22 to enter and mix with the medicament in the medicament chamber 23 as the diluent chamber 22 is reduced in volume because the first plunger 28 continues to move towards the second plunger 29. Preferably, the first stage mechanism is configured to move the first plunger 28 until contacting second plunger 29 in the bulge 32, but lesser or greater movement can be suitable in some embodiments.

Further mixing of the diluent and medicament in the medicament chamber 23 to suspend or dissolve the medicament in the diluent can be accomplished by shaking of the injector 10. In some embodiments, for example the embodiment shown in FIGS. 4 and 5, the outer housing 12 can include a transparent window portion 14 adjacent the medicament chamber 23 such that the user can physically inspect the extent of mixing of the suspension through the window.

At this point, the first stage of operation is completed and the injector 10 is ready for injection of the mixed medicament from the medicament chamber 23. Injection is preferably achieved by completion of a second stage of operation, which uses a second stage mechanism or firing mechanism that includes guard 66, trigger mechanism 52, and ram 60 in this embodiment. The user-operable trigger device to activate the device in both first and second stages of operation can include a single control that is operated in first and second triggering stages, or, as in the preferred embodiments described, can include separate user-manipulable controls that are operated separately from each other. For example, the control to initiate the second stage can be operable once the first stage is completed, but with the second stage mechanism keeping the injector from firing prior to its activation.

The injector 10 includes a trigger mechanism 52 that is preferably housed within the proximal end of the outer housing 12. The trigger mechanism 52 includes a portion of the inner portion or housing 13 that can be attached to the outer housing 12, such as by snaps, an adhesive, a weld, or other known attachment. Trigger protrusions 56 extend radially inwardly from the proximal end of trigger arms 57 and are resiliently biased outwardly. Trigger protrusions 56 form the aperture 58 about the shaft 63 of the ram 60, the shaft 63 being received in the aperture 58. The shaft 63 is preferably at least as long as the longitudinal movement of the ram 60 required in the first stage of operation. Upon movement of the ram 60 in the distal direction during the first stage of operation, the trigger protrusions 56 enter into blocking association with the enlarged end 64 of the ram 60 to prevent further distal movement of the ram 60 prior to the firing of the injector 10 upon actuation of the trigger mechanism 52.

A trigger member of the trigger mechanism 52, such as a latch portion or housing 61, is provided exterior to the inner housing 13 to retain the trigger protrusions 56 in the blocking association with the enlarged end 64 after the first stage of operation to prevent premature firing of the injector 10. The latch housing 61 is slideable inside the outer housing 12 with respect to the inner housing 13, preferably in an axial direction, and the latch housing 61 preferably surrounds the inner housing 13.

The distal end of the outer housing 12 preferably includes a needle guard 66 that is moveable with respect to the outer housing 12. The needle guard 66 is retractable between a protecting position and an injecting position. In the protecting position, the needle 126 is disposed within the guard 66. The needle guard 66 is retractable, preferably into the outer housing 12, in a proximal direction to the injecting position, in which the injection portion 127 of the needle 126 is exposed for insertion into a patient. In the preferred embodiment, the proximal movement of the guard is prevented substantially in the injecting position. The guard 66 is preferably resiliently biased distally towards the protecting position by compression coil spring 72. Also, the needle guard 66 has an axial opening 74 to allow the needle 126 pass there through, and which may be sized according to the type of injector desired. The needle guard 66 extends proximally through the injector 10 and is of unitary with the latch housing 61.

Other embodiments can incorporate alternative trigger mechanisms for actuating firing of the injector. For example, the injector can include a button or other suitable depressible member on the outer housing that, upon depression thereof, actuates firing of the injector.

In the preferred embodiment, the second stage of operation to fire the injector 10 is initiated by retracting the guard 66 to the injecting position, such as by pushing the guard against the patient's skin. The needle guard 66 is associated with the latch housing 61 such that when the guard 66 is displaced proximally, it slides the latch housing 61 also in a proximal direction to release the trigger protrusions 56 from blocking association with the enlarged end 64 of the ram 60. Preferably, the latch housing 61 has a latching portion that abuts the inner housing 13 in an association to bias and maintain the trigger protrusions 56 positioned in the blocking association with the enlarged end 64 prior to the firing of the injector 10. When the latch housing 61 is slid proximally by the retracting of the guard 66 to the injecting position, the latching portion slides beyond the portion of inner housing 13 that it contacts to flex the trigger protrusions 56, allowing the trigger protrusions 56 to move radially outwardly with respect to the shaft 63 and therefore from the blocking association with the enlarged end 64. When this happens, i.e., when the trigger mechanism 52 is actuated, the spring 62 biases the ram 60 against the first plunger 28 to fire the injector 10. The cartridge 18 is configured such that when the first plunger 28 is displaced in a distal direction, the volume of the medicament chamber 23 is decreased, forcing the mixed medicament out therefrom and through the bore of needle 24. Latch housing 61 preferably defines trigger openings adjacent to the latching portions, which are configured to receive a portion of the inner housing 13, such as the surface disposed radially outwardly from the trigger protrusions 56. A same energy source, such as spring 62, can be configured to power both first and second stages.

In the preferred embodiment, the user can push the distal end of the injector 10 against the patient's skin as shown in FIG. 5, pushing the needle 126 into the skin at the injection location, preferably substantially at the same speed as the injector is pushed, although alternative embodiments can move the cartridge forward to insert the needle. Once the needle 126 is fully inserted to an insertion point at a penetration depth in the patient's skin, the trigger mechanism 52 fires the injection of medicament into an injection location.

Preferably, the injecting position of the guard 66 is such that a predetermined length of the end of needle 126 is exposed from the guard 66. In some embodiments, such as where the opening 74 is of a sufficiently large diameter, the skin of the patient maybe allowed to extend into the opening 74 when the device 10 is pressed there against, and a needle that does not protrude beyond the distal end of the guard 66 can be used. In most embodiments, the distance by which the needle tip extends past the distal end of the guard will be fairly close to the depth of the insertion of the needle. Additionally, in some embodiments, the distal surface of the guard can be discontinuous.

The injector 10 can be configured for various types of subcutaneous injections, intradermal injections, intravascular injections, or other types of injections. In the preferred embodiment, the guard 66 is configured to allow insertion of the needle to a penetration depth in the skin that is up to about 5 mm below the skin surface. More preferably, the penetration depth is less than about 4 mm, and in one embodiment is less than about 3 mm. Preferably, the insertion depth is at least about 0.5 mm and more preferably at least about 1 mm. In another embodiment, the distance by which the needle extends past the guard 66 or the distal surface of the guard 66 that contacts the skin is up to about 5 mm, more preferably up to about 4 mm, and in one embodiment up to about 3 mm. Preferably, extension distance is at least about 0.5 mm, more preferably at least about 1 mm, and most preferably at least about 2 mm. In a preferred embodiment, tip 127 of the needle 126 extends by a distance of around 2.5 mm beyond the portion of the guard 66 that contacts the skin in the injecting position. In alternative embodiments, the needle tip stops behind or proximal to the guard, and penetrates the skin that is pushed into the guard.

In another embodiment, such as for intramuscular injection, the injector is configured to allow the needle to be inserted into the patient to a penetration depth in the skin, or alternatively beyond the distal surface of the guard, by a distance of up to about 15 mm. In one embodiment, this distance is about between 10 mm and 14 mm. In an embodiment for jet injection of epinephrine for instance, a preferred penetration depth or distance beyond the guard is between about 12 mm and 13.5 mm, and most preferably around 12.7 mm. Jet injection with this length needle improves the distribution of the medicament in the patient tissue compared to non-jet injection. Other exposed needle lengths can be selected for jet injection to different depths below the skin, with a preferred overall penetration length of between about 0.5 mm and about 20 mm. In these embodiments, the needle guard is preferably configured for retracting from a protecting position, preferably covering the entire needle, to an injecting position, in which the desired length of the end of the needle is exposed.

In some embodiments, the energy source, which is preferably spring 62, and the container, which is preferably cartridge 18, are configured to jet inject the medicament into the patient to an injection site. The spring 62 applies a force on the ram 60 to bias the first plunger 28 that is preferably sufficient to elevate the pressure within the diluent and medicament chambers 22, 23 to a level high enough to eject the medicament from the needle 126 as a jet. Jet injection is to be understood as an injection with sufficient velocity and force to drive the medicament to locations remote from the needle tip 127. The jet injector embodiments deliver a jet injection, the medicament is jet injected distally or in other directions, such as generally radially by the elevated pressure jet, which beneficially improves the distribution of the medicament after the injection and keeps a large bolus from forming that can detrimentally force the medicament to leak back out of the patient around the needle or through the hole left behind by the needle after it is removed. In alternative autoinjector embodiments that use needles, the injection pressures are relatively very low, and the medicament exits the needle tip inside the patient and is typically deposited locally around the needle in a bolus.

Preferably, the needle 127 is between 26 and 28 gage, and are most preferably around 27 gage, but alternatively other needle gages can be used where the other components are cooperatively configured to produce the desired injection. Preferably, the components of the injector 10 are configured to jet inject the medicament to a subterraneous injection site.

Preferred injection rates are below about 0.75 mL/sec., more preferably below about 0.6 mL/sec., and preferably at least about 0.2 mL/sec., more preferably at least about 0.3 mL/sec, and most preferably at least about 0.4 mL/sec. Preferably, the injection of the entire amount of medicament is completed in less than about 4 seconds, more preferably in less than about 3 seconds, and most preferably in less than about 2.5 seconds. Preferably, the medicament injection takes at least about 1 second, and more preferably at least 1.5 seconds, and most preferably at least about 1.75 seconds. A preferred embodiment injects the medicament at about 0.5 mL/sec., completing the injection of 1 mL in about 2 seconds.

The entire amount of mixed medicament contained and injected from the container 18 is preferably between about 0.02 mL and 4 mL, and preferably less than about 3 mL, and in the preferred embodiment is around 1 mL. Larger volumes may also be selected depending on the particular medicament and dosage required. Preferably, the cartridge 18 shown in FIG. 1 is assembled into the remaining parts of the injector 10 already containing the desired amount of diluent and medicament therein. In a preferred embodiment, the container 18 contains about 1 mL of diluent and medicament.

While illustrative embodiments of the invention are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present invention.

What is claimed is:

1. An injector for injecting a medicament into a patient, comprising:
   a container defining:
      a first chamber containing a fluid, and
      a second chamber;
   an injection conduit configured for directing the fluid fired from the container into the patient;
   a transfer mechanism operable by a user to transfer the fluid from the first chamber to the second chamber in a first stage of operation;
   a firing mechanism operable by the user for firing the fluid from the second chamber through the injection conduit in a second stage of operation; and
   an energy source in powering association with the transfer and firing mechanisms to drive the transfer mechanism and the firing mechanism in both the first stage of operation and the second stage of operation,
   wherein the injection conduit has a position that is fluidly isolated from the second chamber, the injector further comprising a transfer control that is manually operable to operate the transfer mechanism in the first stage of operation and to fluidly communicate the injection conduit with the second chamber in the first stage of operation.

2. The injector of claim 1, further comprising an injection trigger mechanism operably associated with the firing mechanism to operate the firing mechanism in the second stage of operation.

3. The injector of claim 2, wherein the transfer and firing mechanisms comprise a firing ram that is movable over a first throw in the first stage of operation and a second throw in the second stage of operation, the energy source in biasing association with the ram in each stage of operation to power the ram.

4. The injector of claim 3, wherein the injection trigger mechanism is configured to block movement of the ram beyond the first throw, the injection trigger being actuatable to release the ram to travel over the second throw.

5. The injector of claim 2, further comprising a retractable guard that is movable between:
- a protecting position in which the injection conduit is disposed within the guard; and
- an injecting position in which an injection needle portion of the injection conduit is exposed for injection of the fluid in the patient;
- wherein the injection trigger mechanism is configured for operating the firing mechanism in the second stage of operation after the retractable guard is retracted from the protecting position.

6. The injector of claim 5, wherein the retractable guard is operably associated with the injection trigger mechanism to cause the injection trigger mechanism to operate the firing mechanism when the guard is retracted to the injecting position.

7. The injector of claim 1, wherein the first stage of operation includes venting the second chamber.

8. The injector of claim 1, wherein the transfer control comprises a cap associated with the container and disposed to cover the injection conduit prior to the first stage of operation, which cap is separable from the injection conduit and container after the first stage of operation.

9. The injector of claim 1, wherein the injection conduit comprises a communicating needle portion, the transfer control operable to relatively move the communicating needle portion with respect to the second chamber to pierce the container to fluidly communicate the second chamber with the communicating needle portion in the first stage of operation.

10. The injector of claim 9, wherein the injection conduit comprises an injecting needle portion disposed and configured to pierce the skin of the patient for assisting the injection of the fluid in the second stage of operation.

11. The injector of claim 10, wherein the energy source and firing mechanism are configured for delivering the fluid by jet injection to an injection site within patient tissue remote from the injecting needle.

12. The injector of claim 9, wherein the injection conduit is configured to deliver the fluid by jet injection into the patient during the second stage of operation to pierce the skin of the patient for assisting the injection of the fluid in the second stage of operation.

13. The injector of claim 9, wherein the transfer control comprises a cap associated with the container and disposed to cover the injection conduit prior to the first stage of operation, which cap is separable from the injection conduit and container after the first stage of operation.

14. The injector of claim 13, further comprising a cap release in locking association with the cap to prevent operation thereof, and being positionable in a release position in which the cap release releases the cap to permit operation thereof in the first stage of operation.

15. The injector of claim 1, wherein the second chamber comprises a medicament, and the fluid comprises a diluent configured for dissolving or suspending the medicament therein for injection into the patient.

16. An injector for injecting medicament into a patient, comprising:
- a container comprising a fluid chamber containing a medicament therein, the fluid chamber comprising a needle hub at the distal end thereof;
- an injection conduit configured for directing the medicament fired from the container into the patient, the injection conduit having a position that is fluidly incommunicated with the fluid chamber;
- a firing mechanism operable by the user for firing the medicament from the fluid chamber through the injection conduit;
- an energy source in powering association with the firing mechanism to drive firing mechanism; and
- a transfer control operable to fluidly communicate the injection conduit with the needle hub of the fluid chamber, the transfer control comprising a cap associated with the container and disposed to cover the injection conduit;
- wherein the cap is separable from the injection conduit upon operating the transfer control to fluidly communicate the injection conduit with the needle hub.

17. The injector of claim 16, wherein the injection conduit comprises a communicating needle portion, the transfer control being operable to relatively move the communicating needle portion with respect to the fluid chamber to pierce the container adjacent the needle hub to fluidly communicate the fluid chamber with the communicating needle portion.

* * * * *